United States Patent [19]
Pelc

[11] Patent Number: 5,533,080
[45] Date of Patent: Jul. 2, 1996

[54] REDUCED FIELD-OF-VIEW CT SYSTEM FOR IMAGING COMPACT EMBEDDED STRUCTURES

[75] Inventor: Norbert J. Pelc, Los Altos, Calif.

[73] Assignee: Lunar Corporation, Madison, Wis.

[21] Appl. No.: 438,138

[22] Filed: May 8, 1995

Related U.S. Application Data

[63] Continuation of Ser. No. 216,235, Mar. 22, 1994, Pat. No. 5,485,492, which is a continuation-in-part of Ser. No. 52,228, Apr. 22, 1993, abandoned, which is a continuation of Ser. No. 860,818, Mar. 31, 1992, abandoned, continuation-in-part of PCT/US93/10903, Nov. 12, 1993.

[51] Int. Cl.⁶ .................................................. G01N 23/00
[52] U.S. Cl. .................................................. 378/5; 378/4
[58] Field of Search .................................................. 378/5, 4

[56] References Cited

U.S. PATENT DOCUMENTS

| | | | |
|---|---|---|---|
| 3,848,130 | 11/1974 | Macovski | 250/369 |
| 3,965,358 | 6/1976 | Macovski | 250/369 |
| 4,029,963 | 6/1977 | Alvarez et al. | 250/360 |
| 4,150,297 | 4/1979 | Broggren | 378/20 |
| 4,506,327 | 3/1985 | Tam | 378/5 |
| 4,541,293 | 9/1985 | Caugant et al. | 74/89 |
| 4,550,371 | 10/1985 | Glover et al. | 364/414 |
| 4,686,695 | 8/1987 | Macovski | 378/146 |
| 4,864,594 | 9/1989 | Inbar et al. | 378/19 |
| 4,887,604 | 12/1989 | Shefer et al. | 128/654 |
| 4,914,588 | 4/1990 | Schittenhelm | 364/413 |
| 5,014,293 | 5/1991 | Boyd et al. | 378/197 |
| 5,049,746 | 9/1991 | Ito | 378/99 |
| 5,155,756 | 10/1992 | Pare et al. | 378/196 |
| 5,287,274 | 2/1994 | Saint Felix et al. | 364/413 |

FOREIGN PATENT DOCUMENTS

| | | |
|---|---|---|
| 3726456 | 4/1988 | Germany. |
| 8713524 | 3/1989 | Germany. |

OTHER PUBLICATIONS

Vertebral Bone Mineral Analysis: An Integrated Approach with CT1, Willi A. Kalendar, Ph.D. 1985 RSNA Annual Meeting.

Generalized Image Combinations In Dual KVP Digital Radiography, A. L. Lehman et al., Med. Phys. 8(5) Sep./Oct. 1981.

*Primary Examiner*—Craig E. Church
*Attorney, Agent, or Firm*—Quarles & Brady

[57] ABSTRACT

A CT apparatus for scanning compact structures associated with a larger body uses radiation source producing a reduced field-of-view to simplify construction and reduce exposure of the larger body. Truncation artifacts in the reconstructed image caused by volume elements in the larger body imaged by the radiation beam only for projections at some angles, are reduced by acquiring two projections at two different energies and combining those projections to compensate for the attenuation of the radiation by the volume elements of the larger body.

8 Claims, 5 Drawing Sheets

REDUCED FIELD-OF-VIEW CT SYSTEM FOR IMAGING COMPACT EMBEDDED STRUCTURES

The present application is a continuation of Ser. No. 08/216,235 filed Mar. 22, 1994, now Pat. No. 5,485,492 which is a continuation-in-part of Ser. No. 08/052,228 filed Apr. 22, 1993, now abandoned which is a file wrapper continuation of Ser. No. 07/860,818 filed Mar. 31, 1992, now abandoned and a continuation in part of PCT/US93/10903 filed Nov. 12, 1993.

FIELD OF THE INVENTION

The present invention relates to the field of radiographic analysis of the human body and, in particular, to a method of measuring and displaying tomographic views of compact structures embedded in the human body.

BACKGROUND OF THE INVENTION

In a computed tomography system ("CT system"), an x-ray source is collimated to form a fan beam with a defined fan beam angle and fan beam width. The fan beam is oriented to lie within the x-y plane of a Cartesian coordinate system, termed the "imaging plane", and to be transmitted through an imaged object to an x-ray detector array oriented within the imaging plane.

The detector array is comprised of detector elements which each measure the intensity of transmitted radiation along a ray projected from the x-ray source to that particular detector element. The detector elements can be organized along an arc, matching the fan beam angle each to intercept x-rays from the x-ray source along a different ray of the fan beam.

The intensity of the transmitted radiation received by each detector element in the detector array is dependent on the attenuation of the x-ray beam along a ray by the imaged object. Each detector element α produces an intensity signal $I_\alpha$ dependent on the intensity of transmitted radiation striking that detector element α.

The x-ray source and detector array may be rotated on a gantry within the imaging plane so that the fan beam intercepts the imaged object at different angles. At each angle, a projection is acquired comprised of the intensity signals from each of the detector elements α. The projections at each of these different angles together form a tomographic projection set.

Normally a projection set will be taken over 360° of gantry rotation, however, it is known to obtain a projection set with as little as 180° plus half the subtended fan beam angle, by making use of the fact that the attenuation of an x-ray by the imaged object is relatively unchanged when the x-rays travel in opposite directions along a single ray. An attempt to reconstruct an image with less than a projection set will normally lead to image artifacts caused by the missing data.

A gantry that may support the x-ray tube and detector array over rotations of more than 180° is costly to construct and can be bulky.

The acquired tomographic projection set is typically stored in numerical form for computer processing to "reconstruct" a slice image according reconstruction algorithms known in the art. The reconstructed slice images may be displayed on a conventional CRT tube or may be converted to a film record by means of a computer controlled camera.

The volume subtended by the fan beam, as intercepted by the detector elements during rotation of the gantry, defines the field-of-view of the CT system.

The amount of data required to reconstruct a CT image is a function of the CT system's field-of-view, the larger the field-of-view, the more data that must be collected and processed by the CT system and thus the longer the time required before an image can be reconstructed. The acquisition of additional data in each projection also increases the cost and number of the components of the CT system.

Therefore, for imaging compact structures within the body, it would be desirable to limit the field-of-view to an angle commensurate with the cross-sectional area of that compact structure. Such a reduction in field-of-view, accompanied by a reduction in the size of the fan beam, would reduce the total dose of x-rays received by the patient. In a CT machine constructed for only imaging compact structures, a reduced field-of-view would reduce the cost of the machine and provide increased image reconstruction speed as a result of the reduced amount of data required to be processed. Also, as is known in the art, smaller field of view images may be reconstructed faithfully using fewer projection angles, thereby further reducing the reconstruction times. The reduced cost of such a machine would result primarily from the reduced number of detectors and associated data handling circuitry required, and from the less powerful image reconstruction processor required to handle the amount of reduced data. Cost savings from a resulting simplified mechanical construction might also be achieved.

Unfortunately, for a CT system to accurately reconstruct images of a compact structure within an attenuating body, it is ordinarily necessary that the entire body containing the compact structure be within the CT system's field-of-view. Even when the only structure of interest is centrally located and its attenuation properties are very different than those of the rest of the section, such as the spine within an abdominal section, conventional CT methods require that substantially the entire object be within the field of view. If the body containing the compact structure extends beyond the field-of-view of the CT system, then projections at some gantry angles will include attenuation effects by volume elements of the body not present in projections at other gantry angles. For the present discussion, these volume elements present in only some projections are termed "external volumes".

In the reconstruction process, the attenuation caused by external volumes is erroneously assigned to other volume elements in the reconstructed image. This erroneous assignment produces artifacts, manifested as shading or cupping, and sometimes as streaks, in the reconstructed tomographic image and are termed "truncation artifacts".

Selective material imaging by use of x-ray transmission measurements at multiple energies is known. However, when used in a CT mode, prior methods acquired data for the entire object.

SUMMARY OF THE INVENTION

The present invention provides a method for reducing the effect of external volumes on the reconstructed image and thus allowing the construction of a reduced field-of-view CT machine, in cases where the goal is to form an image of a compact structure whose attenuation properties differ from those of the rest of the section. The different energy dependence of the attenuation of the compact structure and the body is exploited to produce a projection set reflecting only the compact structure. This projection set is created from a combination of two projection sets taken at different x-ray energies.

Specifically, radiation having first and second energies is projected through the compact structure and portions of the body over the field-of-view and a first and second projection set at the first and second energies is acquired. The first and second projection sets are then combined to produce a third projection set dependent substantially on only the attenuation of the compact structure. This third projection set is reconstructed into an image of the compact structure.

The present invention relies on the realization that external volumes do not contribute to the values in this third projection set, and therefore their absence do not detract from the accuracy of the final image forward from the third projection.

It is thus one object of the invention to reduce the truncation artifacts affecting a reduced field-of-view CT machine in applications where the compact structure to be imaged is embedded in or attached to a second structure outside of the field-of-view of the CT machine, and has differential attenuation properties.

It is another object of the invention to reduce the width of the radiation beam of a conventional CT machine to approximately match the width of a compact structure of interest, thus reducing total patient exposure, without creating unacceptable truncation artifacts.

In one embodiment, the present invention employs a C-arm providing less than 180° of rotation of the x-ray source and detector rather than a conventional gantry. Use of dual energy measurements to eliminate the effect of the portions of the body around the compact structure reduces the image artifacts from these portions thus reducing image artifacts resulting from the acquisition of less than a complete projection set on the C-arm.

Thus it is another object of the invention to permit use of the more versatile and less cumbersome C-arm architecture on a tomographic system.

The use of dual energy measurements permits the elimination of spectral shift artifacts as is taught in U.S. Pat. No. 4,029,963 to Alvarez hereby incorporated by reference. It is thus another object of the invention to further reduce spectral shift artifacts which may be exacerbated by the use of a small field-of-view system or limited projection sets.

Other objects and advantages besides those discussed above shall be apparent to those experienced in the art from the description of a preferred embodiment of the invention which follows. In the description, reference is made to the accompanying drawings, which form a part hereof, and which illustrate one example of the invention. Such example, however, is not exhaustive of the various alternative forms of the invention, and therefore reference is made to the claims which follow the description for determining the scope of the invention.

DETAILED DESCRIPTION OF THE PREFERRED EMBODIMENT

I. Selective Imaging with Two Energies

Figure 1:
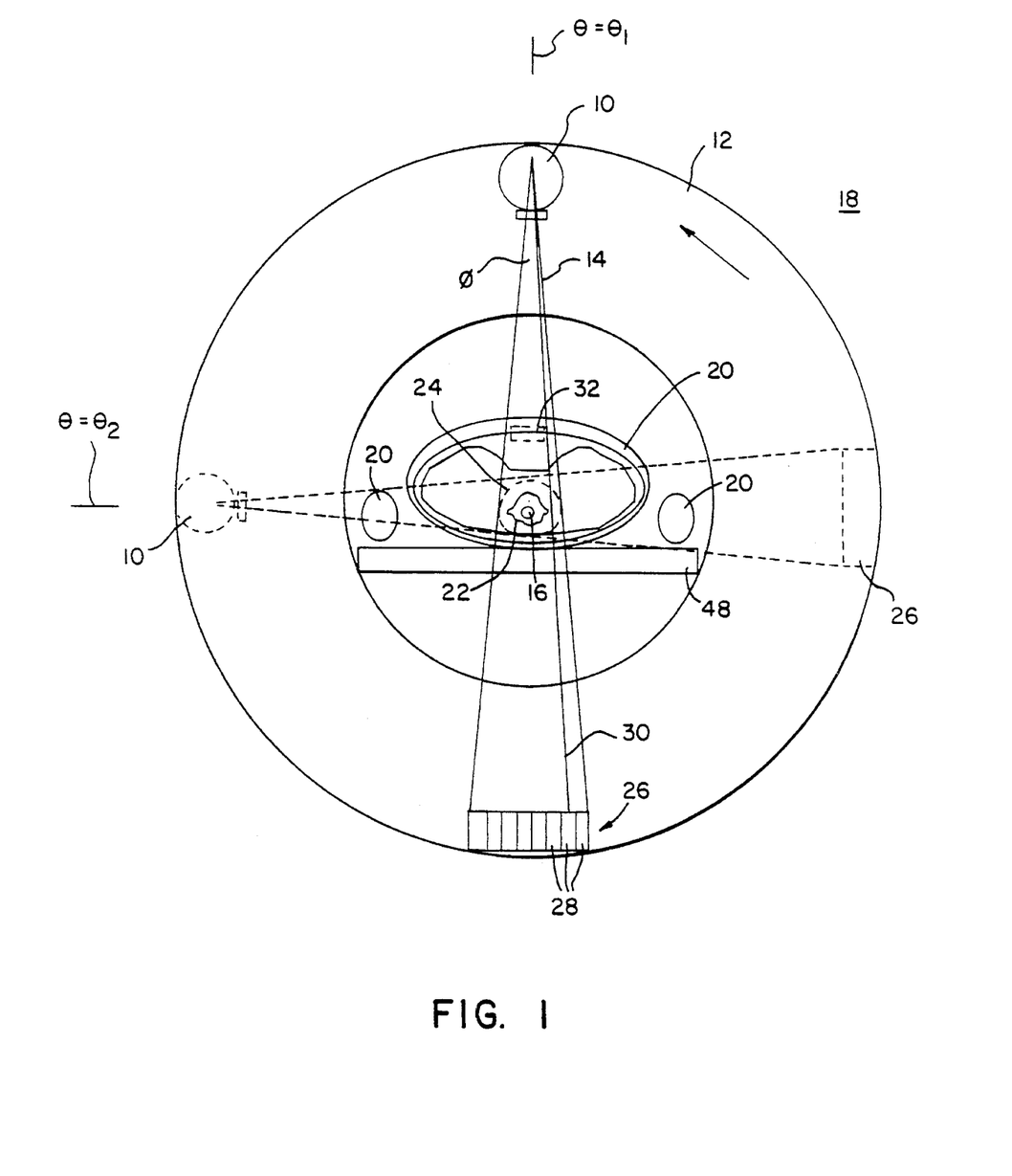
FIG. 1 is a schematic view in elevation of the gantry of a reduced field-of-view CT machine showing "external volumes" within a body surrounding a contrasting compact structure of interest, said external volumes not within the field-of-view of the CT machine but nevertheless attenuating the radiation beam at some gantry angles.

Referring to FIG. 1, a radiation source 10 is mounted on the rim of a generally circular gantry 12 to generate a diametrically oriented fan beam 14 of radiation with a narrow fan angle $\phi$. The gantry 12 is operable to rotate through angles $\theta$ about a center of the gantry 16 within an image plane 18 with the fan beam 14 parallel to the image plane. A patient 20 is positioned at the center of the gantry 16 so that a compact structure of interest 22, such as the spine, is within the field-of-view 24 defined by the volume irradiated by the fan beam 14 at all of a plurality of gantry angles.

The fan beam 14 is received by a detector array 26 having a plurality of detector elements 28 positioned on the gantry 12 opposite to the radiation source 10 with respect to patient 20 and the gantry center 16. Each detector element 28, distinguished by index $\alpha$, measures the intensity $I_\alpha$ of the fan beam 14 attenuated by the patient 20 along a ray 30 of the fan beam 14 at angle $\phi_\alpha$ extending from the radiation source 10 to the center of that detector element 28. The collection of intensity measurements $I_\alpha$, for all detector elements 28 at a gantry angle $\theta$ forms a projection and the collection of projections for all gantry angles $\theta$ forms a projection set.

The fan angle $\phi$ is such as to subtend the compact structure 22 at the plurality of gantry angles $\theta$ but is less than that required to subtend the entire cross section of the patient 20 in the image plane 18. This limited extent of the fan beam 14 significantly reduces the complexity and expense of the detector array 26 and the succeeding processing electronics (not shown in FIG. 1). The limited fan angle $\phi$ of the fan beam 14 also causes certain volume elements 32 ("external volumes") of the patient 20 to contribute to a projection obtained at a first gantry angle $\theta=\theta_1$ but not to contribute to a projection at a second gantry angle $\theta=\theta_2$. As mentioned, these external volumes 32 that are present in only some of the projections of a tomographic projection set create artifacts in the reconstructed image. Generally, all volumes outside of the field-of view 24 are external volumes 32.

The acquisition of two projections at two different energies of radiation from radiation source 10 can be used to eliminate the contribution of these external volumes 32 to the projections, provided that the characteristic attenuation function of the material of the external volume 32 are suitably different from those of the material of the compact structure 22.

MONOENERGETIC IMAGING

If two projections are obtained representing the attenuation of the fan beam 14 along rays 30 by the patient 20 for two radiations energies, these projections may be used to distinguish between the attenuation caused by each of two different basis materials: one material of the external volumes 32 and one material of the compact structure 22. Thus the attenuation of the material of the external volumes 32 and of the compact structure 22 may be determined and the effect of the former eliminated from the projections. The distinction between radiation energy or frequency, and intensity or flux is noted.

The intensity measurement $I_{\alpha 1}$ along a ray $\alpha$ of a first high energy of fan beam 14 radiation will be:

$$I_{\alpha 1} = I_{01} e^{-(\mu_{e1} M_e + \mu_{c1} M_c)} \quad (1)$$

where $I_{01}$ is the intensity of the fan beam 14 of radiation absent the intervening patient 20; $\mu_{e1}$ and $\mu_{c1}$ are the known values of the mass attenuation coefficient (cm$^2$/gm) of the material of external volume 32 and of compact structure 22 respectively at this first radiation energy; and $M_e$ and $M_c$ are the integrated mass (gm/cm$^2$) of external volume 32 and of compact structure 22, respectively.

This equation may be simplified as follows:

$$\ln \frac{I_{01}}{I_{\alpha 1}} = \mu_{e1} M_e + \mu_{c1} M_c \quad (2)$$

The values of $\mu_{e1}$ and $\mu_{c1}$ of equation (1) are dependent on the energy of the radiation of the fan beam 14 and on the chemical compositions of the materials 32 and 22.

As is well known in the art, the values of $\mu_{e1}$ and $\mu_{c1}$ may be measured, or computed, given the chemical composition of the materials.

A second intensity measurement $I_{\alpha 2}$ along the same ray 30, at a second radiation energy, will be given by the following expression:

$$\ln \frac{I_{02}}{I_{\alpha 2}} = \mu_{e2} M_e + \mu_{c2} M_c \quad (3)$$

where $\mu_{e2}$ and $\mu_{c2}$ are different from $\mu_{e1}$ and $\mu_{c1}$, by virtue of the different photon energy, and $I_{02}$ is the incident intensity. Again, $\mu_{e2}$ and $\mu_{c2}$ may be measured or computed.

Equations 2 and 3 are two independent equations with two unknowns, $M_e$ and $M_c$, and may be solved simultaneously to provide values for $M_e$ and $M_c$. For example, $$M_c = \frac{\mu_{e1} L_2 + \mu_{e2} L_1}{\mu_{e1} \mu_{c2} + \mu_{e2} \mu_{c1}} \quad (4)$$

where $$L_1 = \ln \frac{I_{01}}{I_{\alpha 1}} \text{ and } L_2 = \ln \frac{I_{02}}{I_{\alpha 2}}$$

Stable solutions require that $$\frac{\mu_{e2}}{\mu_{e1}} \neq \frac{\mu_{c2}}{\mu_{c1}}$$

This, in turn, results from the different energies of the two beams and from the different chemical compositions of the two materials (fundamentally, different relative contributions of photoelectric absorption and Compton scattering for the two materials).

With knowledge of $M_e$ and $M_c$, the contribution of the external volume 32 may be eliminated by substituting for the intensity measurement $I_{\alpha 1}$ the value $I_{01} e^{-\mu_{c1} M_c}$, or more simply, by using the calculated value $M_c$ directly in the reconstruction algorithms as is understood in the art. The creation and measurement of two monoenergetic radiation beams will be described further below.

POLYENERGETIC IMAGING

Faster imaging requires a stronger radiation source 10, which also often entails an increase in the width of the energy spectrum of the radiation source 10 at each energy E. For such broadband radiation, equations (2) and (3) above, become more complex requiring an integration over the spectrum of the radiation source 10 as follows:

$$I_\alpha = \int I_0(E) e^{-\{M_e \mu_e(E) + M_c \mu_c(E)\}} de \quad (5)$$

Such equations do not reduce to a linear function of $M_e$ and $M_c$ after the logarithm, and hence more complex non-linear techniques must be adopted to evaluate $M_e$ and $M_c$.

One such technique, termed the closed form fit approximates the value of $M_c$ as a polynomial function of the log measurements along ray $\alpha$ at a high and low energy, for example:

$$M_c = k_1 L_1 + k_2 L_2 + k_3 L_1^2 + k_4 L_2^2 + k_5 L_1 L_2 \quad (6)$$

$M_e$ can similarly be computed.

It will be recognized that polynomials of different orders may be adopted instead. The coefficients of the polynomial, $k_1$ through $k_5$, are determined empirically by measuring a number of different, calibrated, superimposed thicknesses of the two materials to be imaged. Alternatively, it is known that the total measured polyenergetic attenuation can be treated as if the attenuation had been caused by two dissimilar "basis" materials. Aluminum and Lucite™ have been used as basis materials. The computed basis material composition is then used to compute $M_e$ and $M_c$. The advantage of this approach is that it is easier to build calibration objects from aluminum and Lucite™ than, for example, bone and soft tissue. The decomposition of an arbitrary material into two basis materials and further details on selective material imaging are described in the article "Generalized Image Combinations in Dual KVP Digital Radiography", by Lehmann et al. Med. Phys. 8(5), Sept./Oct. 1981.

The determination of the coefficients of equation (6) is performed with a radiation source having the same spectral envelopes as the radiation source 10 used with the CT apparatus. The coefficients are determined using a Least Squares fit to the empirical measurements developed with the known thicknesses of the models.

As indicated by the above discussion, the ability to distinguish between two materials 32 and 22, and thus the ability to discount the effect of one such material (32) requires a differential relative attenuation by the materials caused by photoelectric and the Compton effects. This requirement will be met by materials having substantially different average atomic numbers and is enhanced by increased difference in the two energies.

It is possible that the external volumes 32 of the patient 20 will include more than one type of material. An examination of the equations (3) and (4), however, reveals that the above described method will not unambiguously identify the thicknesses of a material in the presence of more than two material types within the patient 20. As a result, the above described method works best when the material of the compact structure 22 and the materials of the partial volumes 32 have sufficiently different attenuation functions so that the variations among tissue types of the external volumes 32 are small by comparison. Examples are where the compact structure 22 is bone and the partial volumes 32 are muscle, water or fat; or where the compact structure contains iodinated contrast agent and the external volumes 32 do not. These limitations are fundamental to dual energy selective material imaging and are not unique to the present use. In any case, errors resulting from the simplifying assumption of their being only two materials in body 20, one for the compact structure 22 and one for the external volumes 32 are low enough to permit the above method to be used for the intended reduction of image artifacts.

II. Dual Energy Reduced Field-of-View CT Apparatus

Figure 2:
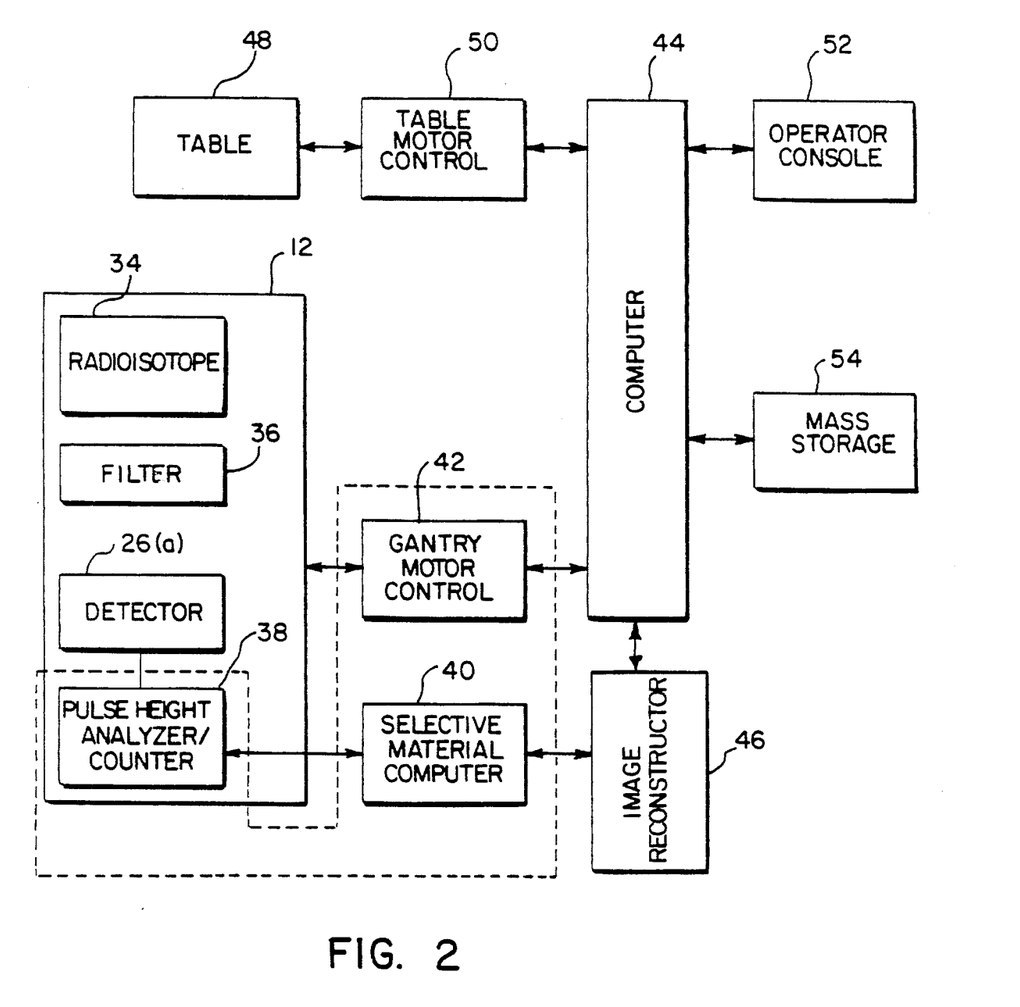
FIG. 2 is a block diagram of a first embodiment of the reduced field-of-view CT system of FIG. 1 useful for practicing the present invention.

Referring now to FIGS. 1 and 2, in a first embodiment CT gantry 12 holds a radioisotope 34 which produces the fan beam of radiation 14 directed toward the patient 20. The radioisotope 34 is preferably a radioactive isotope such as $GD_{153}$, which when filtered by filter 36 prior to the fan beam 14 intercepting the patient 20, produces a fan beam, 14 composed of radiation in one of two distinct and essentially monoenergetic bands. After passing through the patient 20, this radiation is received by a detector array 26(*a*) comprised of a number of detector elements 28 which together receive and detect radiation along each ray 30 of the fan beam 14 to produce separate signals $I_{\alpha 1}$ and $I_{\alpha 2}$ for each detector element α and for each energy of radiation.

The detector 26(*a*) is a scintillating crystal type detector, coupled to a photomultiplier tube, or alternatively a proportional counter using xenon or other high atomic weight gas such as is well understood in the art. Alternatively, the detector array may be a combination photo detector and two scintillating materials atuned to different energy levels. With either such detector 26(*a*), the energy level of the received radiation of the fan beam 14 is measured by a pulse height analyzer 38 which measures the energy deposited by each quantum of radiation, either pulses of light detected by the photodetector in the crystal-type detector 26(*a*) or pulses of charge produced by the proportional counter 26(*a*). The pulse height analyzer 38 characterizes each pulse, by its height, as either high or low energy. The counts of high and low energy pulses for a fixed period of time become the measures $I_{\alpha 1}$ and $I_{\alpha 2}$, respectively. The data for each detector element 28(*a*) is processed by selective material computation circuit 40 which performs the calculations described above (e.g. equation 4), to produce a projection set containing attenuation information for the compact structure 22 only.

The control system of a CT imaging system suitable for use with the present invention has gantry motor controller 42 which controls the rotational speed and position of the gantry 12 and provides information to computer 44 regarding gantry position, and image reconstructor 46 which receives corrected attenuation data from the selective material computation circuit 40 and performs high speed image reconstruction according to methods known in the art. Image reconstructor 40 is typically an array processor in a large field-of-view CT machine, however in the present invention, with a reduced field-of-view, the image reconstruction may be performed acceptably by routines running in a general purpose computer.

Electric communication between the rotating gantry 12 and the selective material computations circuit 40 is via retractable cabling (not shown) which is paid out for a limited number of gantry rotations and then returned to take up spools for the same number of gantry rotations in the other direction.

The patient 20 rests on a table 48 which is radiotranslucent so as to minimize interference with the imaging process. Table 48 is controlled so that its upper surface translates across the image plane 18 and may be raised and lowered to position the compact structure 32 within the field-of-view 24 of the fan beam 14. The speed and position of table 48 with respect to the image plane 18 and field-of-view 24, is communicated to and controlled by computer 44 by means of table motor controller 50. The computer 44 receives commands and scanning parameters via operator console 52 which is generally a CRT display and keyboard which allows the user to enter parameters for the scan and to display the reconstructed image and other information from the computer 44.

A mass storage device 54 provides a means for storing operating programs for the CT imaging system, as well as image data for future reference by the user.

Figure 3:
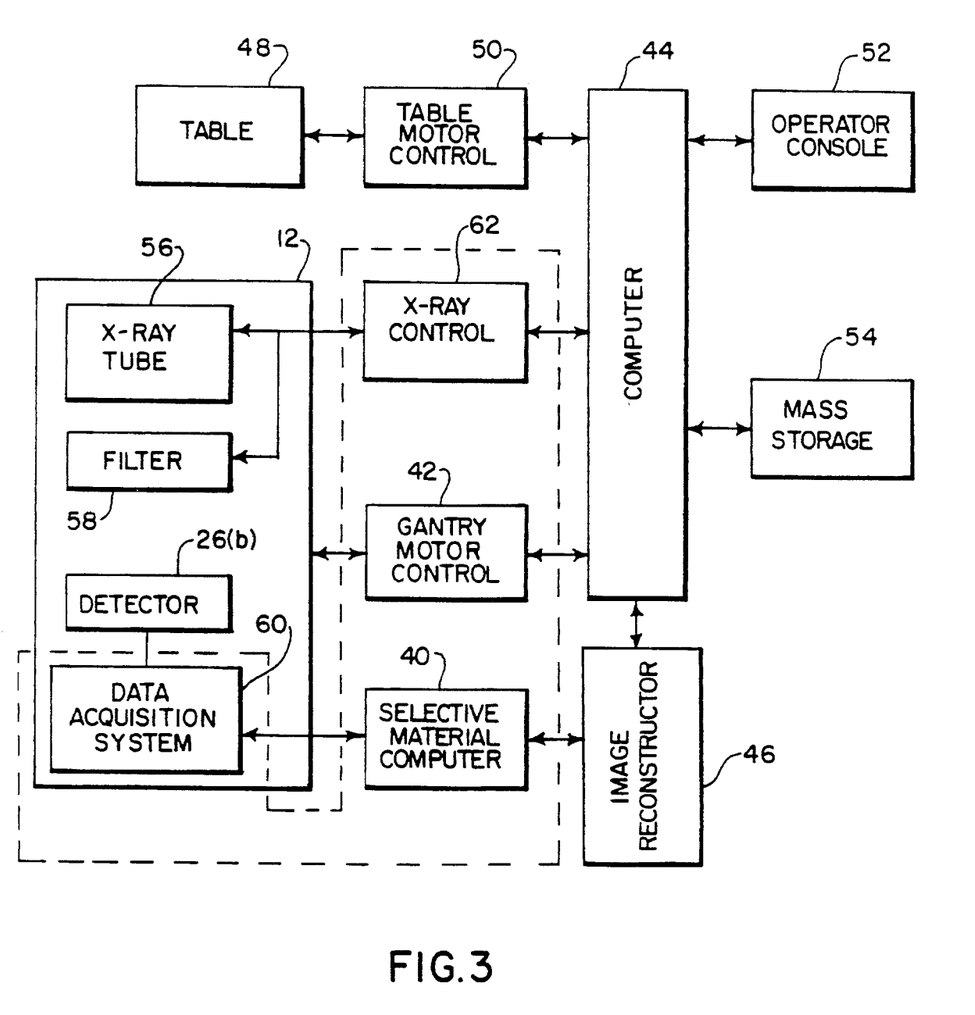
FIG. 3 is a block diagram of a second embodiment of a reduced field-of-view CT system of FIG. 1 useful for practicing the present invention.

Referring to FIGS. 1 and 3, in a second embodiment of the invention, an x-ray tube 56 is held on gantry 12 as the radiation source 10 in place of the radioisotope 34 of FIG. 2. The dual energies of radiation are produced by switching the operating voltage of the x-ray tube 56 as is well understood in the art. Synchronously with the switching of the voltage on the x-ray tube 56, one of two filter materials of filter wheel 58 is rotated into the path of the fan beam 14 on a rotating filter wheel, prior to the beam intercepting the patient 20. The filter materials serve to limit the bandwidth of the polyenergetic radiation from the x-ray tube 56 for each voltage. The filter wheel 58 and the x-ray tube are controlled by x-ray control 62.

A single integrating type detector 26(*b*) employing either a scintillating crystal type detector or a gaseous ionization type detector coupled to an electrical integrator is used to produce the intensity signal, and the integrated signal for each energy level is sampled synchronously with the switching of the bias voltage of the x-ray tube 56 and the rotation of the filter wheel 58, by data acquisition system 60 to produce the two intensity measurements $I_{\alpha 1}$ and $I_{\alpha 2}$ used by the selective material computation circuit 40 employing the polyenergetic corrections technique previously described (e.g. Equation 6).

In all other respects, the CT system in this embodiment is the same as that described for the first embodiment.

Preferably, two projection sets are acquired, one at high x-ray energy, and one at low x-ray energy, at each gantry angle θ before the gantry 12 is moved to the next gantry angle θ in an "interleaved" manner so as to minimize problems due to possible movement of the patient 20. It will be apparent to one of ordinary skill in the art, however, that each projection set may be acquired in separate cycles of gantry rotation, the advantage to this latter method being that the x-ray tube voltage and the filter wheel 58 need not be switched back and forth as frequently or as fast.

Figure 4:
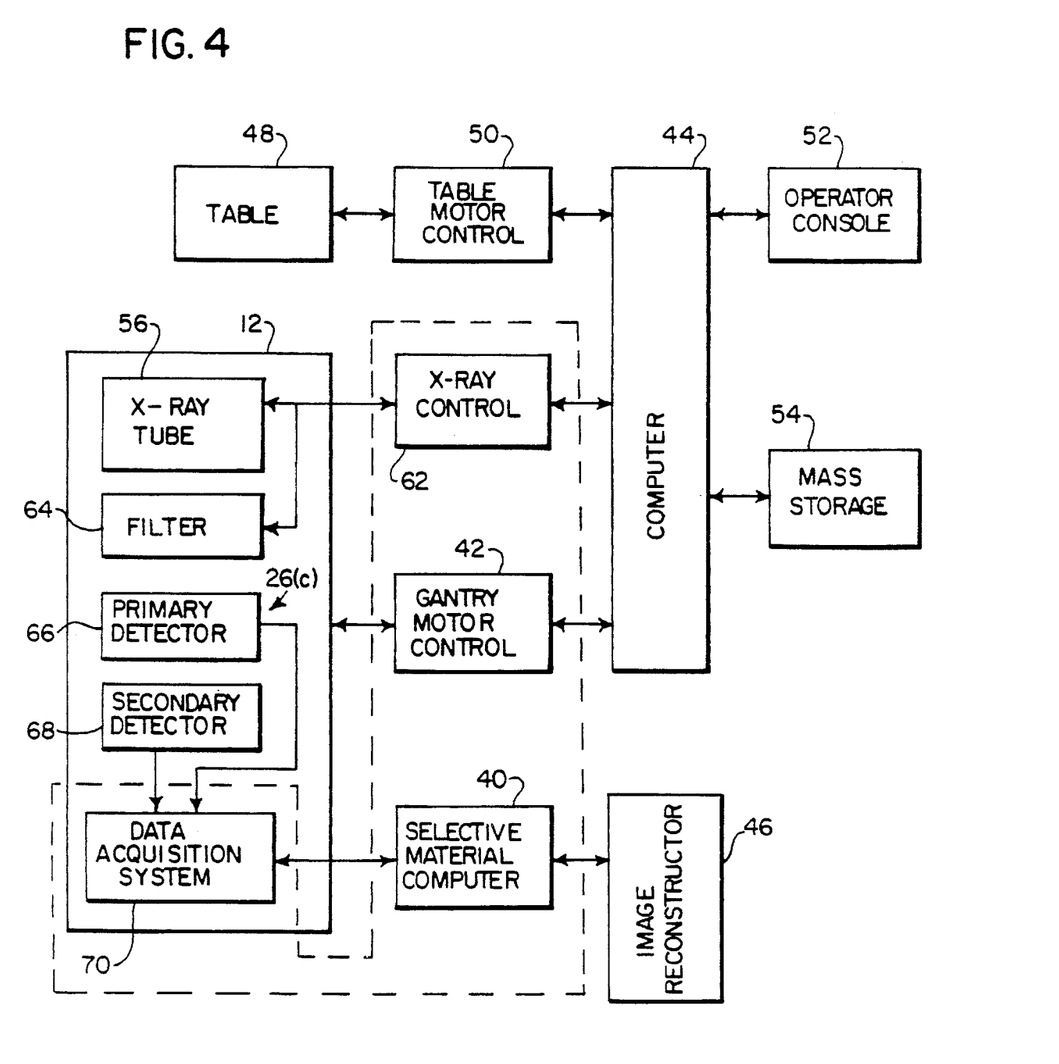
FIG. 4 is a block diagram of a third embodiment of a reduced field-of-view CT system of FIG. 1 useful for practicing the present invention.

Referring to FIGS. 1 and 4, in a third embodiment, the radiation source 10 is an unmodulated x-ray tube 56 producing a polyenergetic fan beam 14 as controlled by x-ray control 62. This fan beam 14 is filtered by stationary filter 64 to concentrate the spectral energies of the x-ray radiation into a high and low spectral lobe. Stationary filter 64 is constructed of a material exhibiting absorption predominantly in frequencies or energy between the two spectral lobes. A detector 26(*c*) is comprised of a primary and secondary integrating type detector 66 and 68 arranged so that the fan beam 14, after passing through the patient 20, passes first through primary detector 66 and then after exiting the primary detector, passes through the secondary detector 68. Each detector 66 and 68 is a gaseous ionization detector filled with an appropriate high atomic number gas such as xenon or a scintillation detector. Relatively lower energy x-ray photons will give up most of their energy in the primary detector 66 and be recorded as the low energy signal $I_{\alpha1}$ for that ray 30 in fan beam 14. These lower energy x-ray have a high probability of interacting in the short distance occupied by the primary detector 66 because the attenuation of the detector is higher at the lower energies. The higher energy photons will give up proportionally more of their energy in the secondary detector 68 and thereby produce the higher energy signal $I_{\alpha2}$. These two signals are collected by a data acquisition system 70 and used to produce selective material projections by circuit 40 using the polychromatic techniques described above, and reconstructed into an image as before.

In all other respects the CT system of the third embodiment is the same as that described for the first embodiment.

Typically projection data will be acquired over 360° of gantry rotation each projection including information on the attenuation of the radiation source for radiation at both of the radiation energies. As is known in the art, however, images may be reconstructed from a "half scan" of projection data acquired over less than 360° of gantry rotation provided at least a minimum gantry rotation of 180° plus the fan beam angle is obtained. Image reconstruction using less than 360° of projection data can further reduce the data required to be processed by the image reconstructor 46. The weighting and reconstruction of images from a half scan data set are discussed in detail in "Optimal Short Scan Convolution Reconstruction for Fanbeam CT", Dennis L. Parker, Medical Physics 9(2) March/April 1982.

Generally, image reconstruction using less than a half scan of projection data will introduce artifacts into the reconstructed image. The severity of these artifacts depends on the amount of missing data and the degree to which the missing data may be estimated or approximated. For certain compact structures where surrounding tissue can be removed by dual energy techniques, it is believed that the small amounts of missing projection data can be tolerated and that less than a half scan of data may be employed, both permitting the use of the more versatile C-arm architecture and further reducing the amount of data needed in the reconstruction also reduces the dose that the patient receives.

Figure 5:
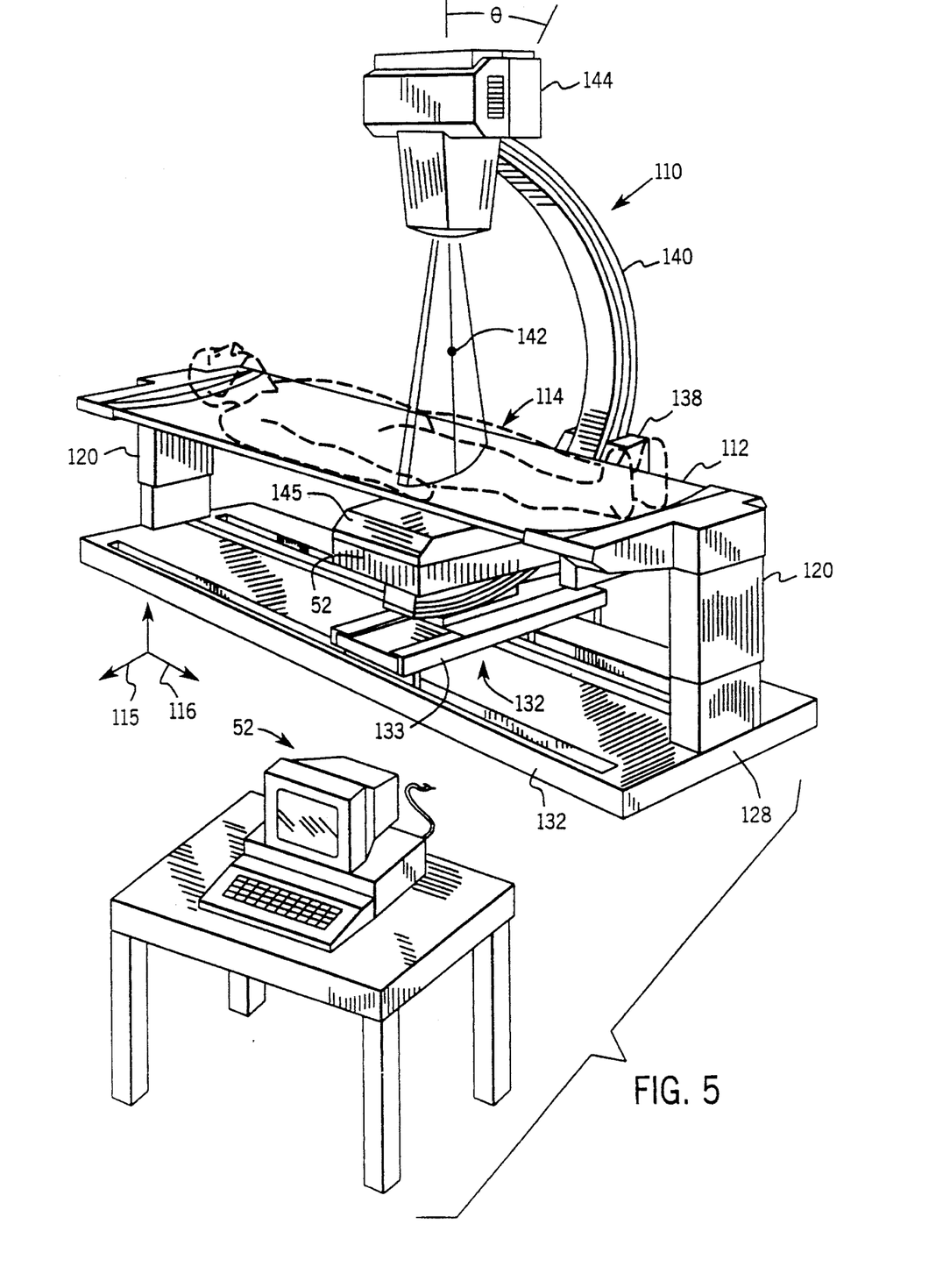
FIG. 5 is a perspective view of a C-arm tomographic system useful for practicing the present invention.

Referring now to FIG. 5, a C-arm radiographic system 110 of a fourth embodiment constructed according to a C-arm architecture, includes a table 112, for supporting a patient 114 in a supine position along a longitudinal or z-axis 116 of a Cartesian coordinate system.

Support pillars 120 hold the longitudinal end of the table 112 and are attached at their bottom ends to a bed 128 supporting the radiographic system 110. The support pillars may telescope to move the table 112 up and down in the y-axis of the Cartesian coordinate system.

The bed 128 includes two longitudinal rails 132 which form a track for supporting a transversely extending gantry pallet 134, and which allow the gantry pallet 134 to be positioned longitudinally along substantially the entire length of the radiographic system 110 along the z-axis 116.

The gantry pallet 134 includes transverse rails 133 carried by rollers (not visible) fitting within the rails 132. Riding on the rails 133 of the gantry pallet 134 is a C-arm collar 138 which may be moved in the x-axis 115 of the Cartesian coordinate system.

Collar 138 is generally arcuate to enclose and slideably hold a C-arm 140 such that the ends of the C-arm may rotate about a center 142 as the body of the C-arm 140 slides through the collar 138. Motion of the C-arm 140 moves the radiation source 144 and detector array 145 about the center 142 by an angle θ. The geometry of the C-arm 140 is such that the angle θ is less than 180° by the width of the collar 138 measured along the C-arm 140.

A radiation source 144 and detector array 145 may be any of those previously described with respect to the first through third embodiments and are mounted so as to produce a fan beam aligned with the plane of rotation of the C-arm 140 and adjustable to subtend a compact structure such as a vertebrae within the patient 114 without significantly illuminating the surrounding tissue.

A radiographic system suitable for use with the present invention is described in further detail in U.S. application No. 07/976,797 entitled: *Patient Positioning Apparatus for Bone Scanning*, assigned to the assignee of the present application and hereby incorporated by reference.

The limitation of the rotation of the C-arm 140 within the collar 138 prevents a half scan of projections from being obtained. As is known in the art, each projection provides data along a line of diameter in a circle of Fourier data used to reconstruct a tomographic image. The missing data results in two pie-shaped opposed sectors of missing Fourier data. This data may be estimated by extrapolating from the data that is obtained. A number of techniques are known in the art. See for example U.S. Pat. No. 4,506,327 to Tam hereby incorporated by reference.

Specifically, for imaging the spine first, projections over the full range of the C-arm 140 are acquired at each of the dual energies. The information of the dual energies is used, as has been described, to create a new projection set including only attenuation data caused by bone and thus primarily data of the vertebrae being imaged. The composition of the soft tissue, used to cancel out the soft tissue image, is determined from rays of one or more projections within the limited angle fan beam know to pass only through soft tissue.

The attenuation data attributable only to bone is then reconstructed using half scan reconstruction techniques with the missing data estimated. Preliminary data indicates that with the removal of the soft tissue, and thus the elimination of artifacts caused by the missing soft tissue, acceptable tomographic images of vertebrae can be obtained with a range of projections obtainable by a C-arm architecture.

It will occur to those who practice the art that many modifications may be made without departing from the spirit and scope of the invention. For example, other similar combinations of the detectors and radiation sources, three of which are described above, may be used to create the dual energy signals $I_{\alpha1}$ and $I_{\alpha2}$. The mechanical structure of the CT apparatus may be based on other well known geometries such as the "translate/rotate" configuration of CT scanner where the radiation source 10 and a detector 26 are translated together across the patient. Also, other energy dependent attenuation effects, for example the k-edge absorption of certain materials such as iodine, may be employed. In order to apprise the public of the various embodiments that may fall within the scope of the invention, the following claims are made.

We claim:

1. A CT machine for imaging bone in vivo comprising:

a patient table sized to receive and support substantially the entire extent of an adult human;

a radiation source collimated to form a beam of x-rays having a width, within a beam plane, substantially less than the width of the patient table but substantially equal to the width of a bone of a supine patient resting against the patient table within the beam plane, the radiation source providing x-rays at a first and second energy directed at the patient table;

a detector, opposing the radiation source about the patient table to produce first and second tomographic data of attenuation measurements associated with the first and energies respectively;

a computational means operating on the first and second tomographic projection set to produce a third tomographic projection set of attenuation measurements depending substantially on only the absorption of x-rays by one of two basis materials;

wherein the one basis material is bone;

means for displaying a tomographic image of bone from the third tomographic projection set.

2. A CT machine as recited in claim 1 wherein the radiation source includes:

an x-ray tube for producing an x-ray beam having multiple energies; and a filter for selectively attenuating the x-rays and transmitting primarily x-rays in two energy bands.

3. A CT machine as recited in claim 1 wherein the radiation source includes:

an x-ray tube for alternately receiving high and low voltage to produce two energies.

4. The CT machine-as recited in claim 1 wherein the radiation source is an x-ray tube providing a broad spectrum of energies and wherein the detector includes a filter for discriminating between high and low x-ray energies.

5. The CT machine as recited in claim 1 wherein the radiation source and detector are mounted on a C-arm for moving the radiation source and detector through the plurality of angles.

6. The CT machine as recited in claim 1 including a C-arm having an arcuate portion with a first and second end, the first end supporting the radiation source and the second end supporting the detector; and a collar slidably supporting the arcuate portion of the C-arm so that the radiation source and detector may rotate through an angle of less than 180° plus an angle subtended by the width of the beam of X-rays.

7. A CT machine for imaging a human vertebra in vivo comprising:

a patient table sized to receive and support an adult human;

a radiation source collimated to form a beam of x-rays having a width, within a beam plane, substantially equal to the width of an adult human vertebra, the radiation source providing x-rays at a first and second energy directed at the patient table;

a detector, opposing the radiation source about the patient table to produce first and second tomographic data of attenuation measurements associated with the first and second energies, respectively;

a computational means operating on the first and second tomographic projection set to produce a third tomographic projection set of attenuation measurements depending substantially on only the absorption of x-rays by one of two basis materials where the one basis material is selected to be bone;

means for displaying a tomographic image of bone from the third tomographic projections set.

8. The CT machine as recited in claim 7 including a C-arm having an arcuate portion with a first and second end, the first end supporting the radiation source and the second end supporting the detector; and a collar slidably supporting the arcuate portion of the C-arm so that the radiation source and detector may rotate through an angle of less than 180° plus an angle subtended by the width of the beam of X-rays.

* * * * *